United States Patent
Xu et al.

(10) Patent No.: US 6,955,716 B2
(45) Date of Patent: Oct. 18, 2005

(54) SELF-HARDENING CALCIUM PHOSPHATE MATERIALS WITH HIGH RESISTANCE TO FRACTURE, CONTROLLED STRENGTH HISTORIES AND TAILORED MACROPORE FORMATION RATES

(75) Inventors: Huakun Xu, Gaithersburg, MD (US); Laurence C. Chow, Potomac, MD (US); Shozo Takagi, Gaithersburg, MD (US); Frederick C. Eichmiller, Ijamsville, MD (US)

(73) Assignee: American Dental Association Foundation, Gaithersburg, MD (US)

(*) Notice: Subject to any disclaimer, the term of this patent is extended or adjusted under 35 U.S.C. 154(b) by 137 days.

(21) Appl. No.: 10/086,484

(22) Filed: Mar. 1, 2002

(65) Prior Publication Data
US 2003/0167093 A1 Sep. 4, 2003

(51) Int. Cl.[7] ............................................. C04B 12/02
(52) U.S. Cl. .................... 106/35; 106/690; 106/691; 106/792; 423/308; 423/309; 423/311; 623/16
(58) Field of Search .................... 106/35, 690, 691, 106/792; 423/308, 309, 311; 623/16

(56) References Cited

U.S. PATENT DOCUMENTS

| | | |
|---|---|---|
| 4,512,038 A | 4/1985 | Alexander et al. |
| 4,655,777 A | 4/1987 | Dunn et al. |
| 4,963,151 A | 10/1990 | Ducheyne et al. |
| 5,181,930 A | 1/1993 | Dumbleton et al. |
| 5,192,330 A | 3/1993 | Chang et al. |
| 5,525,148 A | 6/1996 | Chow et al. |
| 5,545,254 A | 8/1996 | Chow et al. |
| 5,556,687 A | 9/1996 | McMillin |
| 5,652,056 A | 7/1997 | Pepin |
| 5,721,049 A | 2/1998 | Marcolongo et al. |
| 5,766,618 A | 6/1998 | Laurencin et al. |
| 5,976,234 A | 11/1999 | Chow et al. |
| 5,997,624 A | 12/1999 | Chow et al. |
| 6,077,989 A | 6/2000 | Kandel et al. |
| 6,136,029 A | 10/2000 | Johnson et al. |
| 6,207,098 B1 | 3/2001 | Nakanishi et al. |
| 6,214,008 B1 | 4/2001 | Illi |
| 6,281,256 B1 | 8/2001 | Harris et al. |
| 6,281,257 B1 | 8/2001 | Ma et al. |
| 6,287,341 B1 | 9/2001 | Lee et al. |
| 6,376,573 B1 * | 4/2002 | White et al. ................. 523/115 |

FOREIGN PATENT DOCUMENTS

| | | | |
|---|---|---|---|
| DE | 29922585 | * | 8/2000 |

OTHER PUBLICATIONS

"Strong & macroporous calcium phosphate cement" Xu et al., Journal of Biomedical Mat'ls Research (2001), 57(3), p 457–466.*

"A new method to produce macropores in calcium phosphate cements", del Real et al. *Biomaterials* (2002), 23(17) p 3673–3680 (abstract only).*

Miyamoto et al., "Histological and Compositional Evaluations of Three Types of Calcium Phosphate Cements When Implanted in Subcutaneous Tissue Immediately After Mixing", Biomed Rater. Res. [Appl. Biomater.] 48:36–42. Received Feb. 19, 1997; Accepted Jan. 15, 1998.

Chow et al., "Calcium Phosphate Cements", Cements Research Progress, ppg. 215–238, 1999.

(Continued)

Primary Examiner—Paul Marcantoni
(74) Attorney, Agent, or Firm—Banner & Witcoff, Ltd.

(57) ABSTRACT

A bone replacement material and therapy comprises the combination of calcium phosphate compounds and two or more soluble fillers in the form of fibers, mesh or other materials which have the dual functions of reinforcing an in vivo implant while dissolving at a programmed rate to form macropores capable of receiving natural bone ingrowth.

41 Claims, 2 Drawing Sheets

OTHER PUBLICATIONS

Brown and Chow, "A New Calcium Phosphate Water Setting Cement", ppg. 352–379 in Brown, Cements Research Progress, American Ceramic Society, 1986.

Ginebra et al., "Setting Reaction and Hardening of an Apatitic Calcium Phosphate Cement", *J. Dent.Res.* 76:905–912, 1997.

Constantz et al., "Histological, Chemical and Crystallographic Analysis of Four Calcium Phosphate Cements in Different Rabbit Osseous Sites", *J. Biomed. Mater. Res.* [*Appl. Biomater.*] 43:451–461, 1998.

Lee et al., "Alpha–BSM(R): A Biomimetic Bone Substitute and Drug Delivery Vehicle", *Clin. Orthop Rel. Res.* 367:396–405, 1999.

Ishikawa et al., "Reaction of Calcium Phosphate Cements With Different Amounts of Tetracalcium Phosphate and Dicalcium Phosphate Anhydrous", *J. Biomed. Mater: Res.*, 46:504–510, 1999.

Matsuya et al., "Effects of Mixing Ratio and Ph on The Reaction Between $Ca_4[PO_4]_2O$ and $CaHPO_4$", *J. Mater. Sci.:Mater. in Med.* 11:305–311, 2000.

Takagi et al., "Morphological and Phase Characterizations of Retrieved Calcium Phosphate Cement Implants", *J. Biomed Mater. Res.* [*Appl. Biomater.*] 58:36–41, 2001.

Shindo et al., "Facial Skeletal Augmentation Using Hydroxyapatite Cement", *Arch. Otolaryngol. Head Neck Surg.* 119:185–190, 1993.

Sugawara et al., "In Vitro Evaluation of the Sealing Ability of a Calcium Phosphate Cement When Used as a Root Canal Sealer–Filler", *J. Endodont.*, 16: 162–165, 1990.

Chohayeb et al., "Evaluation of Calcium Phosphate as a Root Canal Sealer–Filler Material", *J. Endodont.* 13:384–387, 1987.

Costantino et al., "Experimental Hydroxyapatite Cement Cranioplasty", *Plast. Reconstr. Surg.* 90:174–191, 1992.

Friedman et al., "BoneSource™ Hydroxyapatite Cement: A Novel Biomaterial For Craniofacial Skeletal Tissue Engineering and Reconstruction", *J. Biomed. Mater.Res.* [*appl. Biomater*] 43:428–432, 1998.

LeGeros, "Biodegradation and Bioresorption of Calcium Phosphate Ceramics", *Clin. Mater.* 14:65–88, 1993.

Simske et al., "Porous Materials for Bone Engineering", *Mater. Sci. Forum* 250:151–182, 1997.

Suchanek et al., "Processing and Properties of Hydroxyapatite–Based Biomaterials For Use as Hard Tissue Replacement Implants", *J. Mater. Sci* 13:94–117, 1998.

Xu et al., "Strong and Macroporous Calcium Phosphate Cement: Effects of Porosity and Fiber Reinforcement on Mechanical Properties",*J. Biomed. Mater. Res.* 57:457–466, 2001.

Xu et al., "Reinforcement of a Self–Setting Calcuim Phosphate Cement With Different Fibers",*J. Biomed. Mater. Res.* 52:107–114, 2000.

Xu et al., "Effects of Fiber Length and Volume Fraction on the Reinforcement of Calcium Phosphate Cement",*J. Mater. Sci; Mater. In Med* 12:57–65, 2001.

Von Gonetn et al., "Load–Bearing Behavior of a Simulated Craniofacial Structure Fabricated From a Hydroxyapatite Cement and Bioresorbable Fber–Mesh", *J. Mater. Sci.: Mater. In Med* 11:95–100, 2000.

Takagi et al., "Formation of Macropores in Calcium Phosphate Cement Implants", *J. Mater. Sci.: Mater. In Med.* 12:135–139, 2001.

Chow, "Calcium Phosphate Cements, Chemistry, Properties, and Application", *Mat. Res. Symp. Proc.* 599:27–37, 2000.

Xu et al., "Calcium Phosphate Cement Containing Resorbable Fibers For Short–Term Reinforcement and Macroporosity", *Biomaterials* 23:193–202, 2002.

Chang et al., "Octeoconduction at Porous Hydroxyapatite With Various Pore Configurations", *Biomaterials* 21:1291–1298, 2000.

Matsuya et al., "Effect of Fluoride on Apatite Formation From $Ca_4(PO_4)_2O$ in 0.1 mol $L^{-1}$ $KH_2PO_4$",*J. Mater. Sci.: Mater. In Med.* 9:325–331, 1998.

Shors et al., "Porous Hydroxyapatite, *An Introduction to Bioceramics*", ppg. 181–198 in Hency et al.,*An Introduction to Bioceramics*, World Sci. Pub., NJ, 1993.

* cited by examiner

SELF-HARDENING CALCIUM PHOSPHATE MATERIALS WITH HIGH RESISTANCE TO FRACTURE, CONTROLLED STRENGTH HISTORIES AND TAILORED MACROPORE FORMATION RATES

This invention was made in the course of research supported at least in part by grants from the National Institute of Dental and Craniofacial Research, Grants No. R29 DE12476 and DE11789. Therefore, the Government may have certain rights to the invention.

FIELD OF THE INVENTION

In a principal aspect, the present invention relates to bone substitute replacement materials, particularly calcium phosphate compositions in combination with biodegradable additives that together comprise composites having increased strength, and yet accommodate bone growth methods for use of such bone substitute materials.

BACKGROUND OF THE INVENTION

Several types of self-hardening calcium phosphate compositions have been studied (Brown and Chow, A New Calcium Phosphate Water Setting Cement, pp. 352–379 in Brown, Cements Research Progress, American Ceramic Society, OH, 1986; Ginebra et al., Setting Reaction and Hardening of an Apatitic Calcium Phosphate Cement, *J. Dent. Res.* 76:905–912, 1997; Constantz et al., Histological, Chemical, and Crystallographic Analysis of Four Calcium Phosphate Cements in Different Rabbit Osseous Sites, *J Biomed Mater. Res. [Appl. Biomater.]* 43:451–461, 1998; Miyamoto et al., Histological and Compositional Evaluations of Three Types of Calcium Phosphate Cements When Implanted in Subcutaneous Tissue Immediately After Mixing, *J. Biomed. Mater. Res. [Appl. Biomater.]* 48:36–42, 1999; Lee et al., Alpha-BSM(R): A Biomimetic Bone Substitute and Drug Delivery Vehicle, *Clin. Orthop Rel. Res.* 367:396–405, 1999. Because of its chemical and crystallographic similarity to the carbonated apatitic calcium phosphate mineral found in human bones and teeth, hydroxyapatite has been one of the most often used restorative materials for the repair of human hard tissues. One of the calcium phosphate compositions, developed by Brown and Chow in 1986 and named calcium phosphate cement, or CPC, self-hardens to form hydroxyapatite as the primary product. The term "self-harden" refers to the paste being able to harden by itself. For example, the CPC paste can be placed into a bone cavity and self-harden subsequent to contact with an aqueous medium. CPC typically may be comprised of particles of tetracalcium phosphate (TTCP: $Ca_4(PO_4)_2O$) and dicalcium phosphate anhydrous (DCPA: $CaHPO_4$) that react in an aqueous environment to form solid hydroxyapatite, Ishikawa et al., Reaction of Calcium Phosphate Cements with Different Amounts of Tetracalcium Phosphate and Dicalcium Phosphate Anhydrous, *J. Biomed. Mater: Res.* 46:504–510, 1999; Matsuya et al., Effects of Mixing Ratio and Ph on The Reaction Between $Ca_4[PO_4]_2O$ and $CaHPO_4$, *J. Mater. Sci.:Mater. in Med* 11:305–311, 2000; Takagi et al., Morphological and Phase Characterizations of Retrieved Calcium Phosphate Cement Implants, *J. Biomed. Mater. Res. [Appl. Biomater.]* 58:36–41, 2001.

Calcium phosphate compositions (such as CPC) are highly promising for a wide range of clinical uses due to their excellent biocompatibility, osteoconductivity and bone replacement capability. For example, CPC has been studied for use in the reconstruction of frontal sinus and augmentation of craniofacial skeletal defects (Shindo et al., Facial Skeletal Augmentation Using Hydroxyapatite Cement, *Arch. Otolaryngol. Head Neck. Surg.*, 119:185–190, 1993), endodontics (Sugawara et al., In vitro Evaluation of the Sealing Ability of a Calcium Phosphate Cement When Used as a Root Canal Sealer-Filler, *J. Endodont.* 16:162–165, 1990), and root canal applications (Chohayeb et al., Evaluation of Calcium Phosphate as a Root Canal Sealer-Filler Material, *J. Endodont.* 13:384–387,1987). However, these examples of self-hardening calcium phosphate materials are mechanically weak. That is, the low strength and susceptibility to brittle catastrophic fracture of CPC have severely limited its use to only non load-bearing applications. The use of CPC "is limited to the reconstruction of non-stress-bearing bone" (Costantino et al., Experimental Hydroxyapatite Cement Cranioplasty, *Plast. Reconstr. Surg.* 90:174–191, 1992), and "clinical usage was limited by . . . brittleness . . . " (Friedman et al., BoneSource™ Hydroxyapatite Cement: a Novel Biomaterial for Craniofacial Skeletal Tissue Engineering and Reconstruction, *J. Biomed. Mater. Res. [Appl. Biomater]* 43:428–432, 1998).

The already weak biomaterials are made even weaker when macropores are built into them. In this regard, macropores have been built into biomaterials to facilitate bony ingrowth and implant fixation (LeGeros, Biodegradation and Bioresorption of Calcium Phosphate Ceramics, *Clin. Mater.* 14:65–88, 1993; Simske et al., Porous Materials For Bone Engineering, *Mater. Sci. Forum* 250:151–182, 1997; Suchanek et al., Processing and Properties of Hydroxyapatite-Based Biomaterials for use as Hard Tissue Replacement Implants, *J. Mater. Sci.* 13:94–117, 1998). One advantage of CPC is that it can form macroporous hydroxyapatite implants in situ without involving sintering and machining. But it has been found that macropores degrade the initial implant strength. Studies showed that the strength of CPC, which was already low without macropores, degraded precipitously by an order of magnitude with macropores (Xu et al., Strong and Macroporous Calcium Phosphate Cement: Effects of Porosity and Fiber Reinforcement on Mechanical Properties, *J. Biomed. Mater. Res.*, 57:457–466, 2001). On the other hand, after macroporous materials are implanted, the strength of the implants significantly increases once new bone starts to grow into the macropores (Shors et al., Porous Hydroxyapatite, pp. 181–198 in Hency et al., An Introduction to Bioceramics, World Sci. Pub., NJ, 1993). Therefore, it is in the early stage of implantation when a macroporous CPC type implant is in the most need of strength and toughness.

In other words, the major challenge for brittle materials like calcium phosphate cements is to withstand tensile stresses which can cause catastrophic fracture. This results since most load-bearing situations usually involves tensile stress components. The ability of such material to resist tensile stresses can be characterized in tests of uniaxial tension, bending, flexure, or diametral tension, which are more demanding than compression tests. U.S. Pat. Nos. 5,525,148, 5,545,254, 5,976,234, and 5,997,624 (Chow et al.) disclose cements that achieved strength values in diametral tension for calcium phosphate cements ranging from less than 1 Mpa to less than 10 Mpa (1 Mpa=$10^6$ Neutrons per square meter). This is considered to be too low for useful application of bone replacement in high stress regions in vivo.

Xu et al. suggested fiber reinforcement of calcium phosphate cement in "Reinforcement of a Self-Setting Calcium Phosphate Cement with Different Fibers", *J. Biomed. Mater. Res.* 52:107–114 (2000) and in "Effects of Fiber Length and Volume Fraction on the Reinforcement of Calcium Phosphate Cement", *J. Mater. Sci.: Mater. In Med.* 12:57–65 (2001). Von Gonten et al. suggested a single sheet of mesh reinforcement for calcium phosphate cement in "Load-Bearing Behavior of a Simulated Craniofacial Structure Fabricated from a Hydroxyapatite Cement and Bioresorbable Fiber-Mesh", *J. Mater. Sci.: Mater. In Med.* 11:95–100 (2000). However, there has been no mention of producing macropores in the calcium phosphate cements, and there has been no mention of controlling the strength history and macropore formation rates.

Takagi et al. suggested the formation of macropores resulting from the dissolution of soluble fillers or pore forming agents in "Formation of Macropores in Calcium Phosphate Cement Implants", *J. Mater. Sci.: Mater. In Med.* 12:135–139 (2001). However, the strength in diametral tension decreased to as low as 0.4 Mpa, and there was no mention of controlling the strength history and the rates of macropore formation. Chow reviewed calcium phosphate cements in "Calcium Phosphate Cements: Chemistry, Properties, and Applications", *Mat. Res. Symp. Proc.* 599:27–37 (2000). He mentioned the use of bioresorbable reinforcement fibers and the incorporation of pore forming agents, and acknowledged that "Incorporating macropores into the cement has always led to a significant decrease in mechanical strength", lines 22–23, page 24. There was no mention in his paper of methods that actually increase the strength while producing macropores. There was no mention of fabricating implants with multiple layers with designed functions for each layer for strength or macropores. Xu et al. incorporated fibers and pore forming agents in "Strong and Macroporous Calcium Phosphate Cement: Effects of Porosity and Fiber Reinforcement on Mechanical Properties", *J. Biomed. Mater. Res.* 57:457–466, (2001). Only a single type of fiber was used, which did not lead to, and the authors did not mention, the control of strength history. In addition, only a single type of pore forming agent was used, which did not lead to, and the authors did not mention, the tailoring of the macropore formation rate. Xu et al. used resorbable fibers in "Calcium Phosphate Cement Containing Resorbable Fibers For Short-term Reinforcement and Macroporosity", *Biomaterials* 23:193–202 (2002). Only a single type of fiber was used in each specimen and there was no mention of ways to control the specimen's strength history and macropore formation rates. Furthermore, there was no mention of fabricating implants with multiple layers with specific functions for each layer for strength and macropores in these self-hardening calcium phosphate materials.

U.S. Pat. No. 5,652,056 (Pepin) discloses hydroxyapatite filaments reinforcement. U.S. Pat. No. 6,077,989 (Kandel et al.) discloses condensed calcium phosphate particles. U.S. Pat. No. 6,136,029 (Johnson et al.) discloses bone substitute material comprising of a sintered, load-bearing framework. U.S. Pat. No. 6,287,341 (Lee et al.) discloses ceramic implants comprising an amorphous or poorly crystalline calcium phosphate. None of this prior art mentions methods of combining absorbables fibers or meshes and other stable or degradable fillers of different dissolution rates, or methods of implants with multiple layers having specific functions for each layer, that result in the control of strength histories and the tailoring of macropore formation rates.

U.S. Pat. No. 4,512,038 (Alexander et al.) discloses a composite of a bio-absorbable polymer and carbon fibers. U.S. Pat. No. 4,655,777 (Dunn et al.) discloses a composite of resorbable fibers in a biodegradable polymer matrix. U.S. Pat. No. 4,963,151 (Dueheyne et al.) discloses methods of short and fine fibers distributed homogeneously throughout surgical bone cement. U.S. Pat. No. 5,181,930 (Dumbleton et al.) discloses continuous carbon fibers and a polymer matrix. U.S. Pat. No. 5,192,330 (Chang et al.) discloses oriented fiber reinforcement in a polymer. U.S. Pat. No. 5,556,687 (McMillin) discloses orientations of reinforcing fibers in preforms that are heated and consolidated in a mold. U.S. Pat. No. 5,721,049 (Marcolongo et al.) discloses composites of bioactive glass and ceramic fibers. U.S. Pat. No. 5,766,618 (Laurencin et al.) discloses methods of three-dimensional macroporous polymer matrices that contain hydroxyapatite particulates. U.S. Pat. No. 6,214,008 (Illi) discloses biodegradable implants made of a polymeric biodegradable base material. U.S. Pat. No. 6,281,257 (Ma et al.) discloses three-dimensional porous matrices as structural templates for cells. None of this prior art is related to self-hardening calcium phosphate materials. Furthermore, none mentions methods of combining absorbables fibers or meshes and other fillers of different dissolution rates that result in the control of strength histories and the tailoring of macropore formation rates. In addition, none mentions methods of implants with multiple layers having gradient properties and specific functions for each layer, for example, for strength and/or macropore formation.

U.S. Pat. No. 6,207,098 (Nakanishi et al.) discloses methods of water-soluble polymer or other pore forming agent for producing porous materials. U.S. Pat. No. 6,281,256 (Harris et al.) discloses preparation of porous polymers by a combination of gas forming and particulate leaching steps. None of this prior art reveals methods of strengthening and toughening the materials while producing pores. Furthermore, none mentions methods of combining absorbables fibers or meshes and other fillers of different dissolution rates, or methods of implants with multiple layers having specific functions for each layer, that result in the control of strength histories and the tailoring of macropore formation rates.

In conclusion: (1) There has been no mention in the known prior art of methods of fabricating self-hardening calcium phosphate materials that contain multiple layers with specific functions for each layer for strength and macropore formation, or methods of incorporating, multiple types of fillers and fiber materials with varied dissolution rates for controlled strength histories and tailored macropore formation rates. (2) There has been no mention of methods of effectively and substantially increasing material strength and toughness while producing macropores for vascular and bone ingrowth. (3) There has been no mention in the known prior art of controlling the material strength history and macropore formation rates by mixing absorbable fibers or meshes of fast dissolution rates together with absorbable fibers or meshes of slow dissolution rates. In this way, when the fibers and meshes with faster dissolution rates dissolve and create macropores for bony ingrowth, the fibers and meshes with slow dissolution rates provide longer-term reinforcement. After significant bone ingrowth into the macropores to increase the strength of the implant, the fibers and meshes with slow dissolution rates will then dissolve to create additional macropores for further ingrowth. (4) There has been no mention in the known prior art of self-hardening calcium phosphate materials and implants that contain two or more layers, wherein bone can first grow into a macroporous external layer of the implant, with absorbable fibers or meshes in the second layer providing initial strength but then dissolve to create macropores for further ingrowth, while a strong inner layer with fibers having a slow dissolution rate still maintains reinforcement. Eventually, with significant bone ingrowth into the macropores increasing the implant strength, the slowly-absorbable fibers in the inner layer of the implant dissolve and form macropores for continued bone ingrowth.

SUMMARY OF THE INVENTION

Briefly the present invention comprises bone replacement composites of CPC type materials or compositions mixed with reinforcing, biodegradable elements having controlled dissolution rates and which have the dual function of (1) providing controlled formation of macropores for bone ingrowth and (2) controlled histories of strength and toughness of the composite adequate to support various types of loads or stress during bone ingrowth of natural bone.

Self-hardening calcium phosphate bone replacement or substitute materials thus are combined with various absorbable fibers, meshes or other fillers arranged or incorporated in distinct sections, regions or layers in a substitute bone mass. The composite or combination in the form of a substitute bone mass possesses strength values an order of magnitude higher and toughness two orders of magnitude higher, than those achieved by the prior art. Resulting macroporous scaffolds comprised of the composite encourage bone ingrowth, facilitate implant resorption, and enhance the integration of an implant with adjacent natural bone in vivo. Currently available fabrication and bone replacement techniques can be utilized with the composites of the invention.

Substantially stronger and tougher self-hardening calcium phosphate materials and additive composites or combinations with significantly higher strength, controlled strength histories and tailored macropore formation rates to match application-specific rates of vascular and bone ingrowth result. Implant strength increases as high as 1,000% and work-of-fracture (toughness) increases as high as 10,000% over those achieved by the prior art. Highly-interconnected macropore channels suitable for vascular and bone ingrowth may also be produced in these strong, self-hardening calcium phosphate materials or composites.

In examples, this technology yields self-hardening bone graft materials and functionally graded implants that contain tailored multiple layers or sections with specific functions for each layer or sections for high strength and macropores formation. This technology also incorporates tailored types of fillers and fiber materials (additives) with varied dissolution rates in combination with CPC for controlled strength histories and macropore formation rates. The implant strength history and macropore formation rates are controlled, for example, by using fast-dissolution absorbable fibers together with slow-dissolution fibers or stable fibers. Together these fibers provide a high initial strength to the bone implant. Then the fibers with fast dissolution rates dissolve and create initial macropores for bony ingrowth, while the fibers with slow dissolution rates provide longer-term strength and toughness reinforcement. After significant bone ingrowth into the initial macropores to increase or maintain the strength of the implant, the slow dissolution rate fibers would then dissolve to create additional macropores for further bone ingrowth. In an example of implants with multiple layers, once bone has grown into a macroporous external layer of the implant, the absorbable fibers or meshes in a second layer then dissolve and create highly-interconnected macropores for further ingrowth, while a strong third layer still maintains reinforcement or implant integrity even in a stressful environment. Eventually, with significant bone ingrowth into the macropores associated with a second layer to increase or maintain implant strength, slowly-absorbable fibers in the third layer of the implant dissolve and form macropores for continued natural bone ingrowth and bone structure integrity.

Thus it is an object of the invention to develop strong and tough self-hardening calcium phosphate materials while creating macropores in these materials, via methods of fabricating the materials to contain multiple layers or sections with specific functions for each layer for strength and/or macropore formation, and via methods of incorporating multiple types of fillers and fiber materials with varied dissolution rates for controlled strength histories and tailored macropore formation rates.

Another object of the invention is to provide a means to generate tailored formation of macropores, for example, for bone graft materials and implants to accept vascular and bone ingrowth. The strength history and macropore formation rates are controlled by using, for example, faster-dissolution absorbable fibers coupled with slow-dissolution fibers. Together these fibers provide a high initial strength to the material. Then the fibers with a faster dissolution rate dissolve and create macropores for bony ingrowth, while the fibers with a slow dissolution rate provide longer-term reinforcement. After significant bone ingrowth into the macropores thus increasing or maintaining the strength of the implant, the fibers with a slow dissolution rate will then dissolve to create additional macropores for further ingrowth.

A further object of the invention is to provide a CPC type composite wherein multiple layers can be fabricated. Once bone has grown into a macroporous external layer of the implant, the fast-absorbable fibers, fillers or meshes in a second layer of the implant will dissolve and create highly-interconnected macropores for further ingrowth, while a strong inner layer maintains reinforcement. Eventually, with significant bone ingrowth into the macropores thus increasing the implant strength, the slowly-absorbable fibers in the inner layer of the implant will then dissolve and form macropores for continued ingrowth. Implants with less than or more than three layers can be similarly produced.

These and other objects, advantages and features of the invention will be set forth in the detailed description which follows.

BRIEF DESCRIPTION OF THE DRAWING

In the detailed description which follows reference will be made to the drawing comprised of the following figures.

DESCRIPTION OF THE PREFERRED EMBODIMENT

The term or terms "calcium phosphate" composites, materials or compositions refers to compositions of the type and nature described in U.S. Pat. No. 5,525,148, No. 5,545,254, No. 5,976,234 and No. 5,997,624 and as described in Chow et al. Calcium Phosphate Cements, pp. 215–238 in Cements Research Progress, Struble L. J., editor, Westerville, Ohio; The American Ceramic Society, 1999) that include TTCP containing self-hardening calcium phosphate cements (for example, mixtures of TTCP with DCPA), alpha-tricalcium phosphate (alpha-TCP, $\alpha$-$Ca_3[PO_4]_2$) containing self-hardening calcium phosphate cements (for example, mixtures of alpha-TCP with calcium carbonate, $CaCO_3$), beta-TCP ($\beta$-$Ca_3[PO_4]_2$) containing self-hardening calcium phosphate cements (for examples, mixtures of beta-TCP with hydroxyapatite, $Ca_5[PO_4]_3OH$), and other self-hardening calcium phosphate cements (for example, alkali-containing calcium phosphates like $CaNaPO_4$) by way of example but not limitation, which materials are comprised of calcium and phosphorus compounds in various forms useful as bone or dental implants and substitutes and in the formation of hydroxyapatite. Such references are incorporated herewith by reference as exemplary of such materials but it is to be understood that other such materials will be useful in the practice of the invention in combination with appropriate fibers, meshes, fillers, etc. The term "CPC" may also refer to such materials in general.

The term "fillers" refers to particulates, rods, fibers, ropes, threads, or meshes and substitutes therefore that are incorporated into a material. The term "functionally-graded" refers to the material or combination of bone substitute and filler having several generally independent layers or sections with one or more unique designed functions for each layer, or having a single layer with tailored variations in properties and functions within the material, for example, to provide strength and toughness, or to form macropores at controlled rates to accept vascular ingrowth. The term "dissolution" and other similar terms, such as "soluble" and "degradable", describe materials and fillers that eventually dissolve in a certain environment, for example, bone graft materials or suture materials in a physiological (in vivo) environment. A related term, "absorbable", means that the materials or fillers can be dissolved and absorbed by the environment, as in the examples of surgical absorbable suture materials. For convenience, in the present invention, "fast dissolution" describes fillers that, under physiological conditions, dissolve and create pores in a time period generally ranging from 30 minutes to 1 week. "Medium dissolution" describes fillers that dissolve and create pores in a time period ranging generally from 1 week to 12 weeks. "Slow dissolution" describes fillers that dissolve and create pores in a time period ranging generally from 12 weeks to two years. "Stable" or "non-degradable" fillers maintain their reinforcement for the calcium phosphate bone graft materials for longer than two years.

The types of fibers useful in the practice of the invention may include glass fibers, ceramic fibers, polymer fibers, organic material fibers, metal fibers, or mixtures thereof. The fibers can be in aligned forms or in a random form or array in the CPC matrix, or in a unidirectional, mesh, tape, woven, thread, rope, or other useful forms. The fibers include stable fibers, and degradable fibers with different dissolution rates. The length of fibers incorporated into the materials varies from about 10 $\mu$m (1 $\mu$m=$10^{-6}$ m, "m" stands for meter) for short whiskers up to about 10 m for long fibers. When long fibers that are degradable are mixed into the calcium phosphate material, they can provide the needed reinforcement for a period of time, and then dissolve to create interconnected long channels for vascular and bone ingrowth. The fiber volume fraction in the material, which is the volume of fibers divided by the volume of the composite, varies from about 1% to about 90%, preferably from 5% to 70% and most preferably 20% to 60%. The fiber diameter ranges from 0.1 $\mu$m for small whiskers to 1 mm for large-diameter fibers, preferably from 10 $\mu$m to 500 $\mu$m. For particulate fillers and rod fillers, the particle diameter ranges from 0.1 $\mu$m to 1 mm, preferably from 10 $\mu$m to 500 $\mu$m.

An example of the construction of this invention will be to incorporate two different types of fibers into one of the self-hardening calcium phosphate materials, CPC. The strength history and macropore formation rates of the material are controlled by incorporating a type of absorbable fiber of a relatively fast dissolution rate together with a type of absorbable fibers of a relatively slow dissolution rate. Together these fibers provide a high initial strength to the implant. In the examples of this invention, the strength the self-hardening calcium phosphate material is increased by as much as 1,000%. Then the fibers with a fast dissolution rate dissolve and create macropores for vascular and bone ingrowth, while the fibers with a slow dissolution rate provide longer-term reinforcement. After significant bone ingrowth into the macropores increasing the strength of the implant, the fibers with a slow dissolution rate will then dissolve to create additional macropores for further bone ingrowth. In addition, non-degradable fibers can also be incorporated into the material together with soluble fillers for stable reinforcement together with macropores for vascular ingrowth.

Porous materials with random pore geometry generally have much smaller interconnecting fenestration than the pores themselves. Therefore, the interconnection size is a limiting factor for osteoconduction, rather than the pores themselves (Chang et al., Osteoconduction at Porous Hydroxyapatite with Various Pore Configurations, *Biomaterials* 21:1291–1298, 2000). To better control the interconnecting fenestration of the macropores, absorbable meshes rather than individual and random arranged fibers may be used to reinforce the materials to provide short-term strength and then to create highly-interconnected macropores after mesh dissolution. As an example, one mesh sheet on the potential tensile side of the self-hardening calcium phosphate implant can reinforce shell structures such as for the reconstruction of parietal skull defects. Several sheets of mesh can also be stacked on the prospective tensile side of the implant for strengthening and then dissolved to create an external macroporous layer to accept bone ingrowth. Stacking mesh sheets in a bone cavity, with the bone graft material filling the pores between the meshes, can achieve the maximum strength and then create interconnected macropores throughout the implant. Furthermore, implants with multiple layers and functionally-graded properties can also be fabricated.

During bone growth into the macroporous external layer of the implant, the absorbable meshes in the second layer would continue to provide substantial strength and toughness before dissolution. The meshes then dissolve to create highly-interconnected macropores for further ingrowth, while a strong inner layer or section of the implant with absorbable fibers of slow dissolution rates maintains reinforcement. Eventually, with significant bone ingrowth into the macropores increasing the implant strength, the slowly-absorbable fibers in the inner layer of the implant will dissolve and form macropores for continued ingrowth. The fiber and mesh and other types of fillers may include inorganic fillers such as ceramics and oxides, metals such as titanium fibers and meshes, and organic fillers such as biodegradable polymers and biologies to prevent infection. The layers may overlap, by arrayed one on top of the other, or arranged in a pattern which itself is an array or matrix designed for maximizing a bone growth pattern deemed most appropriate for the situation. For example a series of concentric cylindrical layers may be provided. Alternatively a honeycomb pattern of layers or sections may be provided. Other patterns are also possible.

The following are examples of the invention:

General Procedure

One of the self-hardening calcium phosphate materials, CPC, is used in this example. Tetracalcium phosphate (TTCP, $Ca_4[PO_4]_2O$) powder is mixed with dicalcium phosphate anhydrous (DCPA, $CaHPO_4$) powder to form the calcium phosphate cement powder. When mixed with a water-based liquid, the calcium phosphate cement self-hardens to form solid hydroxyapatite. A prescribed amount of fibers is mixed with a prescribed amount of calcium phosphate powder and liquid into a paste. (Note the power and fibers may be premixed before adding liquid or at the time of adding the liquid.) The paste is placed into a prepared bone cavity or into a specimen mold. In the case of a specimen mold, the paste in the mold is kept at 100% relative humidity, and the paste self-hardens into a solid specimen containing hydroxyapatite.

EXAMPLE 1

Fabrication

An example of use of this invention is dental, craniofacial and orthopedic bone repair. A calcium phosphate powder is randomly mixed with soluble fillers and pore forming agents such as mannitol crystals ($CH_2OH[CHOH]_4CH_2OH$). The mixture is then mixed with a liquid (water) into a paste. The mannitol crystals can quickly dissolve to produce macropores for vascular and bone ingrowth. Also mixed into the paste are absorbable fibers (for example, Vicryl suture, polyglactin 910 (copolymer of glycolide and lactide) Ethicon, Somerville, N.J.) to provide substantial strengthening and toughening while tissue is growing into the initial macropores resulting from mannitol crystal dissolution. The absorbable fibers themselves can then dissolve and create additional macropores for further ingrowth. Also mixed into the paste are absorbable fibers with a slow rate of dissolution (for example, Panacryl™ suture (copolymer of lactide and glycolide), Ethicon, NJ) so that they can provide longer-term reinforcement while the absorbable fibers with a faster dissolution rate dissolve and create macropores. By the time the fibers with a slow dissolution rate dissolve, the bone will heale, at least in part, and grown into the implant macropores. Bone ingrowth increases implant strength, which will offset the strength decrease from fiber degradation. The fibers can be oriented to resist potential stressor and vectors of tensile stresses, or be distributed as mesh or rope on the prospective tensile side, or be randomly mixed throughout the implant. The fibers can also be in a prior fabricated form to serve a strong core or as an insert for the graft CPC material. Other types of soluble fillers, pore forming agents and fibers of different dissolution rates can also be used in the combination.

EXAMPLE 2

Fabrication

Another example of manufacture comprises bone graft materials with multiple layers. Layered implants can be functionally-graded, by providing tailored layers with graded functions, or by using a single layer with a controlled gradient or variation in functions within the layer. For example, for an implant with several layers, the external layer may contain fillers or fibers with fast dissolution rates to provide a high initial strength and then quickly create macropores to accept vascular ingrowth. The second layer contains fillers or fibers with slow dissolution rates for strength, and then dissolve to form macropores after bone growth into the first layer. Bone ingrowth increases the implant strength, which would offset the strength decrease from fiber degradation. The third layer contains fillers or fibers with slower dissolution rates, or even stable fibers, for longer-term reinforcement for the implant. By the time the fillers or fibers with slow dissolution dissolve, the bone will heal and grown into the implant's macropores. Similar functionally-graded graft materials and implants with less than or more than three layers can also be produced.

EXAMPLE 3

Fabrication

As another example of manufacture of the invention, functionally-graded bone graft materials containing layered structures are prepared with either flat layers or curved layers. An example of curved layers would be a cylindrical implant, having an external surface layer reinforced with fast-dissolution fillers or fibers for macropores to accept vascular ingrowth. The second layer of the cylindrical implant contain fillers or fibers with medium-dissolution rates for short-term strength, which then dissolve to form macropores after bone growth into the first or external surface layer. The strong core of the cylindrical implant contains slow-dissolution fillers or fibers, or even stable fibers, or a strong fabricated insert such as a titanium pin or a ceramic rod, for longer-term reinforcement. Other functionally-graded graft materials and implants containing flat or curved layers with less than or more than two or three layers can be similarly produced to have controlled strength histories and tailored macropore formation rates.

EXAMPLE 4

Fabrication

Another example of manufacture comprises implants with multiple fiber and filler layers for controlled strength history and tailored macropore formation, where the matrix material is CPC. The external layer contains the calcium phosphate cement paste which is mixed with soluble fillers such as mannitol crystals that can quickly dissolve to produce macropores for vascular and bone ingrowth. The second layer of the implant is comprised of the calcium phosphate paste mixed with absorbable fibers (for example, Vicryl suture, polyglactin 910, Ethicon, Somerville, N.J.) to provide substantial strengthening and toughening while tissue is growing into the macropores from mannitol in the external layer of the implant. The absorbable fibers then dissolve and create macropores for further ingrowth. The third layer of the implant is comprised of the calcium phosphate cement paste mixed with absorbable fibers with a slow dissolution rate (for example, Panacryl suture, Ethicon, NJ) so that they can provide substantial reinforcement while the absorbable fibers with a medium dissolution rate dissolve and create macropores.

EXAMPLE 5

Fabrication

Another example of manufacture of this invention comprises implants that contain multiple fibers and filler layers with substantial strengthening, controlled strength history and tailored macropore formation, using different types of self-hardening calcium phosphate matrix materials. These matrix materials include TTCP containing self-hardening calcium phosphate cements (for example, mixtures of TTCP with DCPA), alpha-tricalcium phosphate (alpha-TCP, $\alpha$-$Ca_3$[$PO_4$]$_2$) containing self-hardening calcium phosphate cements (for example, mixtures of alpha-TCP with calcium carbonate, $CaCO_3$, beta-TCP ($\beta$-$Ca_3$[$PO_4$]$_2$) containing self-hardening calcium phosphate cements (for example, mixtures of beta-TCP with hydroxyapatite, $Ca_5$[$PO_4$]$_3$OH, and other self-hardening calcium phosphate cements (for example, alkali-containing calcium phosphates like $CaNaPO_4$). The external layer contains soluble fillers, for example, mannitol crystals, sodium phosphate crystals ($Na_2HPO_4$), sodium bicarbonate ($NaHCO_3$), sugar granules, calcium carbonate, calcium citrate, calcium sulfate hemihydrates, dicalcium phosphate, and beta-dicalcium phosphate. The second layer of the implant contains fillers such as absorbable fibers (for example, Vicryl suture, polyglactin 910, Ethicon, Somerville, N.J.). The third layer of the implant contains fillers such as absorbable fibers with a slow dissolution rate (for example, Panacryl suture, Ethicon, NJ) so that they can provide substantial reinforcement while the absorbable fibers with a medium dissolution rate dissolve and create macropores. Other functionally-graded implants containing flat or curved layers with less than or more than three layers can be similarly produced.

EXAMPLE 6

Fabrication

Another example of manufacture would comprises pre-mixed pastes of calcium phosphate materials containing fillers such as soluble particles and absorbable fibers of various dissolution rates. "Pre-mixed" means that the paste is mixed and stored, for example, in a syringe or a bottle, before being delivered and applied, for example, into a bone cavity or a mold to harden. The pre-mixed pastes include a mixture of TTCP and DCPA, alpha-dicalcium phosphate ($Ca_3$[$PO_4$]$_2$) and calcium carbonate ($CaCO_3$), DCPA and calcium hydroxide (Ca[OH]2), and mixtures thereof. The pre-mixed paste can be used to fill the entire cavity or make single implants. Alternatively, several different types of pre-mixed pastes can be used to make layered structures with tailored functions for each layer. The external layer may contain fast soluble fillers, for example, mannitol crystals, sodium phosphate crystals ($Na_2HPO_4$), sodium bicarbonate ($NaHCO_3$), and sugar granules. The second layer of the implant can contain fillers such as absorbable fibers (for example, Vicryl suture, polyglactin 910, Ethicon, Somerville, N.J.). The third layer of the implant may contain fillers such as absorbable fibers with a slow dissolution rate (for example, Panacryl™ suture, Ethicon, NJ) so that it can provide substantial reinforcement while the absorbable fibers with a medium dissolution rate dissolve and create macropores. Similar functionally-graded graft materials and implants with less than or more than three layers can also be provided.

EXAMPLE 7

Fabrication

Another example of manufacture of this invention comprises self-hardening layered implants with mesh layers for substantial strengthening, controlled strength history, and highly interconnected macroporous scaffolds. Both biodegradable meshes (for example, polyglactin mesh, Ethicon, NJ) and non-degradable meshes (for example, titanium mesh) can be incorporated into calcium phosphate cement together with other fillers, for example, mannitol crystals with a fast rate of dissolution. Once bone has grown into the macroporous external layer, the fillers in the second layer would then dissolve and create macropores for further bony ingrowth, while the strong third layer still maintains reinforcement. Eventually, with significant bone ingrowth into the macropores increasing the implant strength, the fibers with a slow dissolution rate in the third layer would then dissolve and form macropores for continued ingrowth. The fillers with a fast dissolution rate can be soluble mannitol; they will dissolve and create macropores in a couple of days. The fillers in the second layer with an medium dissolution rate can be the absorbable mesh (for example, polyglactin mesh, Ethicon, NJ); the mesh will provide substantial reinforcement for nearly four weeks and then dissolve to create highly interconnected macropores. The fillers in the third layer can be a slow-absorbable suture fiber (Panacryl, Ethicon, NJ). It is a relatively strong suture fiber and can provide strength for nearly 6 months, by which time bone healing will be substantially complete and substantial bone ingrowth will have already occurred. Bone graft materials with less than or more than three layers with flat or curved layers can be similarly produced.

EXAMPLE 8

Fabrication

Another example of manufacture of this invention comprises bone graft materials containing different fillers with substantial reinforcement and tailored macropore formation, where the calcium phosphate material is modified with biodegradable polymers. Biodegradable polymers, both in a liquid form or in a powder form, can be incorporated into the calcium phosphate material, and then the paste can be hardened into a solid. The external layer of the implant contains fast soluble fillers such as mannitol to produce macropores. The second layer of the implant is comprised of absorbable fibers (for example, Vicryl suture, polyglactin 910, Ethicon, Somerville, N.J.) to provide substantial strengthening while tissue is growing into the macropores from mannitol in the external layer of the implant. The absorbable fibers then dissolve and create macropores for further ingrowth. The third layer of the implant is comprised of absorbable fibers with a slow dissolution rate (for example, Panacryl suture, Ethicon, NJ) so that they can provide substantial reinforcement while the absorbable fibers with a medium dissolution rate dissolve and create macropores. Bone graft materials and implants with less than or more than three layers with flat or curved layer shapes can be similarly produced. Additional additives may be incorporated in the mix including biologics, sterilizing agents, pharmacologic compounds, marking agents, accelerators, and combinations thereof.

EXAMPLE 9

Fabrication

Another example of manufacture of this invention comprises implants with different fillers for substantial strengthening, controlled strength history and interconnected macroporous scaffolds, where the fibers are not layered but are mixed in the bone graft material in a random manner. Once bone has grown into the macropores from the fillers with a fast rate of dissolution, the fibers and fillers with a medium dissolution rate will then dissolve and create macropores for further bony ingrowth, while the strong fibers with a slow rate of dissolution or the stable fibers still maintain reinforcement. The fillers with a fast dissolution rate can be the soluble mannitol or other soluble fillers. The fillers in the second layer with a medium dissolution rate can be absorbable meshes (for example, polyglactin mesh, Ethicon, NJ); they will provide substantial reinforcement for weeks and then dissolve to create highly interconnected macropores. The fillers in the third layer with a slow rate of dissolution can be slow-absorbable suture fibers (for example, Panacryl, Ethicon, NJ). It is a relatively strong suture fiber and can provide strength for nearly 6 months, by when bone healing would have completed and substantial bone ingrowth would have already occurred. Bone graft materials and implants with less than or more than three types of fillers and fibers with different rates of dissolution can be similarly produced.

EXAMPLE 10

Fabrication

Another example of manufacture of this invention comprises incorporation of fibers and fillers for controlled strength history and macropore formation, where the calcium phosphate matrix material is modified to be non-rigid or elastomeric (able to deform considerably without brittle fracture). For certain applications, such as periodontal repair, it is desirable to have a highly osteoconductive material like calcium phosphate cement in a non-rigid elastomeric matrix. This is because when rigid calcium phosphate cement is used in periodontal bone repair, tooth mobility results in early displacement and fracture and eventual exfoliation of the hard and brittle implants. A non-rigid calcium phosphate cement will provide compliance for tooth motion without fracturing and displacing the implant. Chitosan (beta-(1,4)-2-amino-2-deoxy-D-glucose, or poly-D-glucosamine, or poly N-acetyl-D-glucosamine) and its derivatives are good candidates for the non-rigid or elastomeric agent. These natural biopolymers are biocompatible, biodegradable and osteoconductive. Both chitosan and absorbable fillers and fibers can be incorporated into the self-hardening calcium phosphate to provide substantial strengthening and toughening, higher deformability without fracture, controlled strength history and highly interconnected macroporous scaffolds resulting from fiber and filler dissolution. Non-rigid or elastomeric implants with less than or more than three layers with flat or curved layer shapes can thus be produced. Non-rigid or elastomeric implants containing randomly mixed fillers and fibers with different rates of dissolution can also be fabricated possessing controlled strength history and tailored rates of macropore formation. The calcium phosphate materials can also contain gelling agents to cause more rapid hardening of the cement or to resist the paste from washout by fluid. These gelling agents include, but are not limited to hydroxypropyl methylcellulose, carboxyl methylcellulose, starch, proteoglycans, and glycoproteins.

EXAMPLE 11

Fabrication

Another example of manufacture of this invention comprises self-hardening calcium phosphate with fibers and fillers for controlled strength history and highly interconnected macropores, where the matrix has varied TTCP/DCPA ratios for rapid dissolution/resorption.

Calcium phosphate cements with TTCP/DCPA molar ratios of less than 1 can set to form Ca deficient hydroxyapatite with residual DCPA, and possess faster dissolution rates. Faster rates of dissolution and resorption are clinically beneficial. Alternatively, the bone graft matrix may be a calcium phosphate cement with varied powder:liquid ratio. This provides pastes with varied viscosity for specific applications and flowable pastes for syringe delivery and injection, with increased porosity at lower powder:liquid ratios, thereby increasing the cement dissolution and resorption rates. Bone graft materials and implants with less than or more than three layers with flat or curved layer shapes can be produced using these calcium phosphate materials. These bone graft materials can alternatively contain randomly mixed fillers and fibers with different rates of dissolution for controlled strength history and tailored rates of macropore formation.

EXAMPLE 12

Fabrication

Another example of manufacture of this invention comprises self-hardening calcium phosphate compositions with absorbable and non-absorbable fibers and fillers for controlled strength history and tailored macropore formation, where the materials are fabricated as pre-forms, which means that they are hardened in molds and then used clinically. With pre-forms, pressure and/or heat can be used to control the material properties and porosity. Bone graft materials and implants with several types of fibers and meshes and other fillers can be mixed together in the calcium phosphate compositions, or functionally-graded and layered structures containing less than or more than three layers with flat or curved layer shapes can be produced as pre-forms.

EXAMPLE 13

Data

Tetracalcium phosphate (TTCP) powder is synthesized from $CaHPO_4$ (dicalcium phosphate anhydrous, or DCPA) and $CaCO_3$ (Baker Analyzed Reagents, J. T. Baker Chemical Co., NJ), which are mixed and heated at about 1500° C. in a furnace (Model 51333, Lindberg, Watertown, Wis.). The heated mixture is quenched and ground to obtain TTCP powder of particle size ranging from 1 $\mu$m to 100 $\mu$m, preferably from 5 $\mu$m to 30 $\mu$m. The DCPA powder is ground to obtain powder of particle size ranging from 0.1 $\mu$m to 100 $\mu$m, preferably from 0.5 $\mu$m to 10 $\mu$m. Then the TTCP and DCPA powders are mixed to form the CPC powder. Water-soluble mannitol ($CH_2OH[CHOH]_4CH_2OH$) crystals of size from 10 $\mu$m to 1 mm, preferably from 50 $\mu$m to 500 $\mu$m, are used to produce macropores in CPC. Other fillers and pore forming agents can be similarly used. The mannitol crystals can be mixed with CPC powder at mannitol/(mannitol+CPC powder) mass fractions ranging from 5% to 85%, preferably from 20% to 70%. In this example, a fraction of 30% is used.

Figure 1:
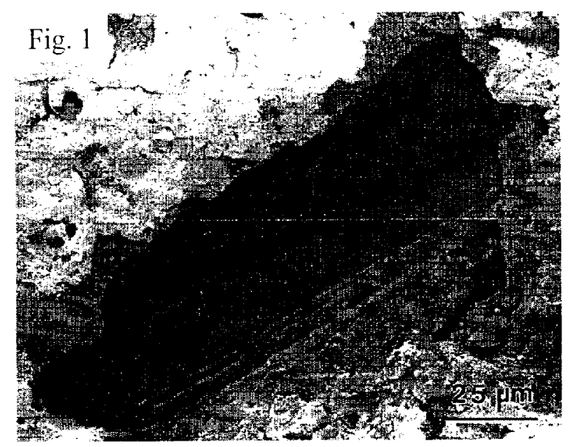
FIG. 1 is a scanning electronmicrograph (SEM) of well-formed macropores in calcium phosphate cement created by the dissolution water-soluble mannitol crystals after immersion in a simulated physiological solution for one day where the macropores are in the shapes of the entrapped water-soluble but dissolved crystals.
Figure 2:
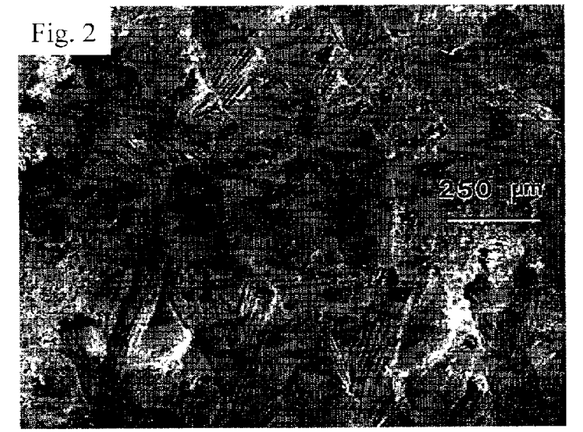
FIG. 2 is a SEM of macropore channels produced in hardened calcium phosphate cement from the dissolution of absorbable fiber meshes after immersion in a physiological solution for twelve weeks.
Figure 3:
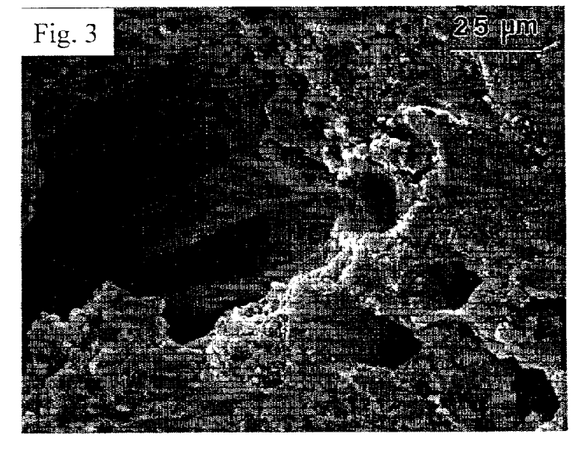
FIG. 3 is a SEM of macropores in hardened calcium phosphate cement from the dissolution of absorbable meshes is shown at a higher magnification.
Figure 4:
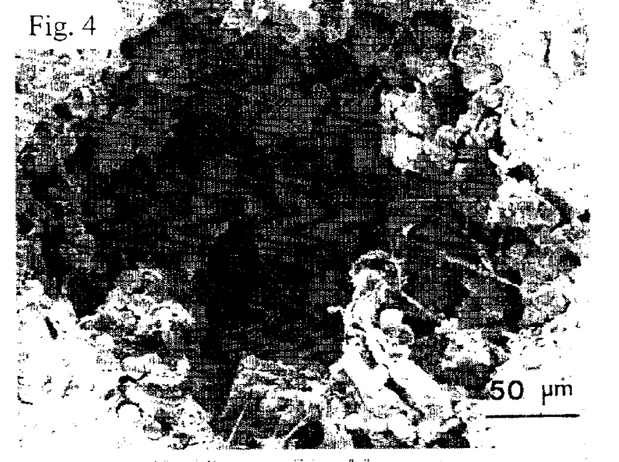
FIG. 4 is a SEM of macropores in calcium phosphate cement resulting from the degradation of absorbable fibers where the specimen has been immersed in a physiological solution for eight weeks and the fibers are partially degraded but are still present.
Figure 5:
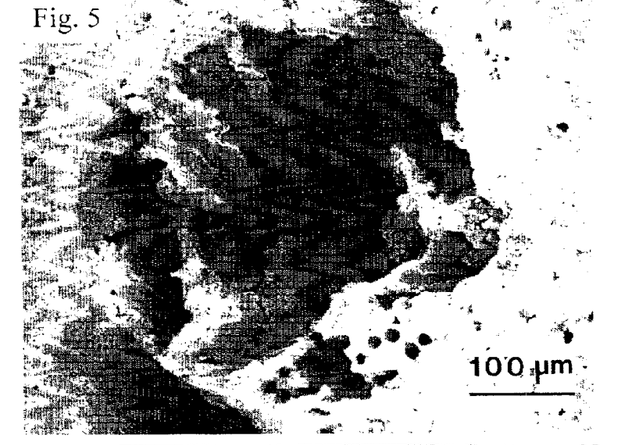
FIG. 5 is a SEM of macropores in calcium phosphate cement resulting from the dissolution of absorbable fibers after immersion in a physiological solution for twelve weeks.
Figure 6:
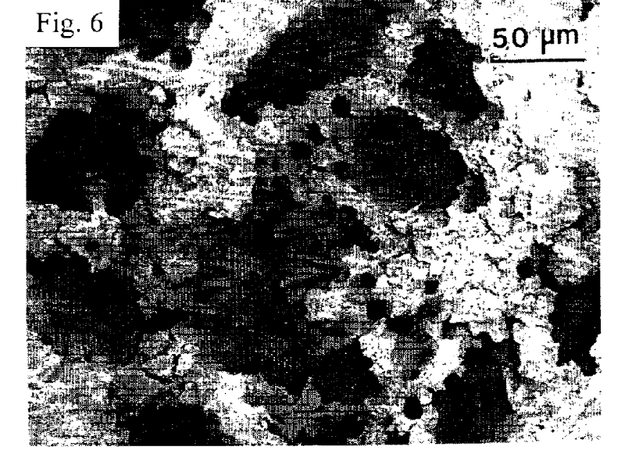
FIG. 6 is a SEM of various appearances of macropores in calcium phosphate cement resulting from the dissolution of absorbable fibers after immersion in a physiological solution for twelve weeks.

When water is used as the cement liquid in mixing with the CPC powder, the cement set in about 30 min. Faster setting is achieved when a $Na_2HPO_4$ solution is used as the cement liquid, in which event the paste hardened in about 5 min. In this example, a model functionally-graded three layer system is fabricated with the first layer being CPC containing 30% mannitol to quickly create macropores for vascular and bone ingrowth (see FIG. 1). The second layer is CPC containing absorbable meshes (Ethicon, NJ) to provide strength and then create highly-interconnected macropores (see FIGS. 2 and 3). The third layer is CPC with Vicryl™ braided suture fibers (Ethicon, NJ) to provide substantial reinforcement. The suture fibers will degrade after significant bone ingrowth in vivo into the macropores from mannitol thus increasing the implant's strength (see FIGS. 4–6). The model specimen dimensions are 3 mm×4 mm×25 mm, with each layer taking approximately 1 mm thickness. The paste of each layer is placed into the specimen mold sequentially, and the composite is self-hardened in a humidor at 100% relatively humidity at 37° C. The control is the same CPC containing 30% mannitol, with the same specimen dimensions. The properties of the specimens after one day immersion in a physiological solution are measured using a standard three-point flexural test and are listed in Table 1.

TABLE 1

Mechanical properties of a functionally-graded three-layer implant and a one-layer control (mean ± standard deviation [sd]; 4 repeats)

| | Flexural Strength (MPa) | Work-of-fracture (Toughness; kJ/m) | Elastic Modulus (GPa) |
|---|---|---|---|
| Three layers; mannitol + mesh + absorbable fibers | 27.9 ± 7.3 | 3.36 ± 0.75 | 3.63 ± 1.25 |
| One layer control: mannitol | 2.0 ± 0.2 | 0.0044 ± 0.0004 | 1.14 ± 0.15 |

The properties of the functionally-graded three-layer implant are significantly higher than those of the control (Student's t; $p<0.05$).

EXAMPLE 14

Data

A model functionally-graded three layer system is fabricated with the first layer being CPC containing 30% mannitol and the second layer being CPC containing absorbable meshes (Ethicon, NJ). The third layer is CPC containing a polymer fiber (Kevlar® 49 (aramid fiber), DuPont Advanced Fibers Systems, Wilmington, Del.). The specimen dimensions are 3 mm×4 mm×25 mm, with each layer taking approximately 1 mm thickness. The paste of each layer is placed into the specimen mold sequentially, and the composite is self-hardened in a humidor at 100% relatively humidity at 37° C. The first layer possesses macropores in about a day from mannitol dissolution to accept vascular ingrowth, while the other two layers with fibers provide substantial strength and toughness. After bone ingrowth into the first layer increasing the implant strength, the absorbable meshes in the second layer then dissolve to create highly-interconnected macropores for further bone ingrowth (see FIGS. 2 and 3), while the third layer with polymer fibers serve as a strong core and provide long-term reinforcement while bone grows into the first and second layers of the implant. The control is the same CPC containing 30% mannitol with the same specimen dimensions. The properties of the specimens after one day immersion in a physiological solution are measured using a standard three-point flexural test and are listed in Table 2.

TABLE 2

Mechanical properties of a functionally-graded three-layer implant and a one-layer control (mean ± sd; 4 repeats)

| | Flexural Strength (MPa) | Work-of-fracture (Toughness; kJ/m) | Elastic Modulus (GPa) |
|---|---|---|---|
| Three layers; mannitol + mesh + polymer fibers | 20.6 ± 6.9 | 2.98 ± 1.29 | 1.83 ± 0.28 |

TABLE 2-continued

Mechanical properties of a functionally-graded three-layer implant and a one-layer control (mean ± sd; 4 repeats)

| | Flexural Strength (MPa) | Work-of-fracture (Toughness; kJ/m) | Elastic Modulus (GPa) |
|---|---|---|---|
| One layer control: mannitol | 2.0 ± 0.2 | 0.0044 ± 0.0004 | 1.14 ± 0.15 |

The properties of the functionally-graded three-layer implant are significantly higher than those of the control (Student's t; $p<0.05$).

EXAMPLE 15

Data

A model functionally-graded two layer system is fabricated. The first layer is CPC containing 30% mannitol to quickly create macropores for vascular ingrowth. The second layer is CPC containing absorbable meshes (Ethicon, NJ). The meshes will provide substantial strengthening while bone is growing into the first layer. After significant bone ingrowth into the first layer thus increasing the strength of the implant, the meshes dissolve to create highly-interconnected macropores to ensure further bone ingrowth into the entire implant. The specimen dimensions are 3 mm×4 mm×25 mm, with the first layer taking 0.5 mm and the second layer taking 2.5 mm. The paste of each layer is placed into the specimen mold sequentially, and the composite is self-hardened in a humidor. The control is the same CPC containing 30% mannitol with the same specimen dimensions. The properties of the specimens after one day immersion in a physiological solution are measured in standard three-point flexure and are listed in Table 3.

TABLE 3

Mechanical properties of a functionally-graded two-layer implant and a one-layer control (mean ± sd; 4 repeats)

| | Flexural Strength (MPa) | Work-of-fracture (Toughness; kJ/m$^2$) | Elastic Modulus (GPa) |
|---|---|---|---|
| Three layers; mannitol + mesh + polymer fibers | 17.5 ± 4.0 | 3.41 ± 1.06 | 1.57 ± 0.46 |
| One layer control: mannitol | 2.0 ± 0.2 | 0.0044 ± 0.0004 | 1.14 ± 0.15 |

The strength and work-of-fracture (toughness) of the functionally-graded two-layer implant are significantly higher than those of the control (Student's t; $p<0.05$).

EXAMPLE 16

Data

Calcium phosphate cement specimens containing 30% mannitol have a total porosity of nearly 70% volume fraction. Macropore lengths of 50 μm to 1000 μm can be produced from the dissolution of mannitol. Another method to produce macropores in calcium phosphate cement is to incorporate absorbable fibers that also increase the strength and toughness. The calcium phosphate paste is mixed with an absorbable fiber (Vicryl™, braided suture, Ethicon, NJ) at 35% volume fraction with a fiber length of 3 mm. The specimens have a flexural strength of (7.2±1.3) MPa, a work-of-fracture (toughness) of (0.4±0.1) kJ/m$^2$, and a modulus (stiffness) of (2.2±0.7) GPa. Macropore channels of a diameter of approximately 300 µm and a relatively large length of 3 mm are produced in hardened calcium phosphate cement after fiber dissolution.

EXAMPLE 17

Data

Another example of this invention uses different types of fibers. These fibers substantially strengthen and toughen the calcium phosphate materials. A calcium phosphate paste is mixed with ceramic silicon carbide fibers using a fiber length of 75 mm and a 10% volume fraction. The self-hardened specimens have a high flexural strength of (33±7) MPa, a work-of-fracture (toughness) of (21.1±4.1) kJ/m$^2$, and a modulus (stiffness) of (5.4±1.7) GPa.

When polymer fibers are incorporated into calcium phosphate cement, the specimens with a relatively high total porosity volume fraction of 63% possess a flexural strength of (14±4) MPa, a work-of-fracture (toughness) of (2.3±0.5) kJ/m$^2$, and a modulus (stiffness) of (2.4±0.5) GPa.

EXAMPLE 18

Data

Another example of this invention couples a modification of the matrix with the reinforcement of absorbable fibers for strength and then macropores for vascular ingrowth. Four systems were studied: calcium phosphate cement as control; calcium phosphate cement+chitosan for deformability; calcium phosphate cement+absorbable mesh for strength and then interconnected macropores; and calcium phosphate cement+chitosan+mesh. The flexural strength values for these four systems are: (3.3±0.4) MPa, (12.0±0.8) MPa, (21.3±2.7) MPa, and (43.2±4.1) MPa, respectively, which are significantly different from each other (Tukey's multiple comparison test; family confidence coefficient=0.95). The strength from chitosan+mesh is dramatically increased over those with chitosan only or with mesh only. A small modification of the matrix with chitosan has a big effect on the composite when coupled with mesh reinforcement. Interconnected macropore channels of diameters of approximately 200 micrometer to 400 micrometers are created in hardened calcium phosphate cement after mesh dissolution.

EXAMPLE 19

Data

Another example comprises a flowable paste of calcium phosphate cement for ease of filling the cavity contours or for syringe delivery, that can self-harden for form implants with controlled strength histories and tailored rates of macropore formation to guide tissue ingrowth. The term "flowable" means here that the paste is relatively thin and can easily flow. As an example, a CPC paste at a powder to liquid ratio of 1 is mixed into a flowable paste and self-hardened to form specimens of 3 mm×4 mm×25 mm as control specimens. Another flowable paste is mixed with chitosan at 15% mass fraction and then mixed with an absorbable fiber (Vicryl, braided suture, Ethicon, NJ) and self-hardened into specimens of the same dimensions. The fiber length is 3 mm and the fiber volume fraction in the specimen is 50%, in order to create a relatively high macropore volume fraction of 50%, with macropore channels of a diameter of nearly 300 µm and a length of 3 mm. Alternatively, mannitol crystals or other soluble fillers can be incorporated into the paste to quickly create macropores for vascular ingrowth. Absorbable fiber meshes can also be mixed into the paste to create highly-interconnected macropores. The mechanical properties of the flowable control specimens and the specimens with 15% chitosan and 50% absorbable fibers are listed in Table 4.

TABLE 4

Mechanical properties of specimens from flowable pastes for ease of filling the cavity contours or for syringe delivery (mean ± sd; 4 repeats)

|  | Flexural Strength (MPa) | Work-of-fracture (Toughness; kJ/m$^2$) | Elastic Modulus (GPa) |
|---|---|---|---|
| CPC + chitosan + absorbable fibers | 6.04 ± 1.87 | 0.36 ± 0.15 | 0.46 ± 0.22 |
| CPC control | 0.47 ± 0.09 | 0.0013 ± 0.0006 | 0.22 ± 0.04 |

The properties of the CPC+chitosan+absorbable fibers are significantly higher than those of the control (Student's t; $p<0.05$).

In review calcium phosphate compounds or calcium phosphate cement, either powder and/or liquid or flowable form comprise a part of the composite bone replacement material. Among the calcium phosphate compounds deemed acceptable for use with this material and in the process of bone replacement are the following which are compatible with an in vivo environment:

TABLE 5

Potential self-hardening calcium phosphate materials or cements:

1. TTCP based self-hardening calcium phosphate cements (for example, mixtures of TTCP with DCPA).
2. Alpha-tricalcium phosphate (alpha-TCP, $\alpha$-Ca$_3$[PO$_4$]$_2$) based self-hardening calcium phosphate cements (for example, mixtures of alpha-TCP with calcium carbonate, CaCO$_3$).
3. Beta-tricalcium phosphate (beta-TCP, $\beta$-Ca$_3$[PO$_4$]$_2$) based self-hardening calcium phosphate cements (for example, mixtures of beta-TCP with hydroxyapatite, Ca$_5$[PO$_4$]$_3$OH).
4. DCPA-based or DCPD-based self-hardening calcium phosphate materials, for example, mixtures of DCPA with calcium hydroxide, Ca(OH)2.
5. Amorphous calcium phosphate-based self-hardening calcium phosphate materials.
   (The term amorphous refers to the material being not crystalline or being poorly crystalline.)

A second important part of the combination is the macropore forming material. Two or more of these macropore forming materials are included in the composite which ultimately serves as the bone replacement item or material. These filler materials are generally categorized in four categories and listed as follows:

TABLE 5-continued

Category 1

1. Fast Dissolution Rate Materials:
   Particles, fibers, mesh or ropes of glass, ceramics, polymers, or mixtures thereof, that, under physiological conditions, dissolve and create pores in time period ranging from 30 minutes to one week.
2. Medium Dissolution Rate Materials:
   Particles, fibers, mesh or ropes of glass, ceramics, polymers, or mixtures thereof, that, under physiological conditions, dissolve and create pores in time period ranging from one week to twelve weeks.
3. Slow Dissolution Rate Materials:
   Particles, fibers, mesh or ropes of glass, ceramics, polymers, or mixtures thereof, that, under physiological conditions, dissolve and create pores in time period ranging from twelve weeks to two years.
4. Stable or Nondegradable Materials:
   Particles, fibers, mesh or ropes of glass, ceramics, polymers, metals, or mixtures thereof, that, under physiological conditions, do not dissolve in a time period of two years.

Various combinations and permutations of the above-listed materials may be included in the composite. As set forth in the examples the composite may comprise layers or separate sections or gradients thereof in a bone graft or bone replacement element. The macropore materials comprise fillers, fibers, meshes, and other material geometries as described. Further, the macropore materials may be mixed or may be segregated into the separate regions of the item comprising the bone graft and bone replacement item. In any event, the mixture may be customized for the application and projected environment.

Further, numerous additional additives may be included as discussed in general. Including those items set forth in Table 6 hereinafter:

TABLE 6

Additional additives:

1. Non-rigid or elastomeric agents, for example, chitosan and its derivatives. Non-rigid or elastomeric agents enable the composite to deform extensively without fracture.
2. Fast-hardening agents, for example, sodium phosphate solution $Na_2HPO_4$. Fast-hardening agents increase the rate of hardening of the paste.
3. Gelling agents, for example, hydroxypropl methylcellulose, carboxyl methylcellulose, starch, proteoglycans, and glycoproteins. Gelling agents cause more rapid hardening of the cement or resist the past from being washed out by fluids such as water and blood (anti-washout).

These described materials may be nixed as set forth in the examples to provide a customized bone replacement material comprised of a calcium phosphate synthetic bone (with or without various additives) and in the form of the hard tissue being repaired plus fillers mixed therein to enhance stress tolerance and to dissolve so as to form macropore passages in different patterns and at different rates as designed for the particular situation.

While various combinations of calcium phosphate materials and fillers arrayed in various layers, sections and mixtures have been disclosed as a bone or hand tissue replacement and whereas various techniques and methods of use of such materials or combinations have been disclosed, alternatives are within the scope of the invention, and the invention is, therefore, limited only by the following claims and equivalents thereof.

What is claimed is:

1. A bone material and hard tissue replacement material comprising, in combination, a mixture of:
   a calcium phosphate compound that forms a chemically compatible in vivo bone or hard tissue replacement composition; and
   at least first and second macropore forming materials, said first and second macropore forming materials each have a dissolution rate in vivo, at least one of said macropore forming materials characterized by increasing the strength value of said mixture in vivo by at least about one order of magnitude relative to a control comprising said compound.

2. The mixture of claim 1 wherein the macropore forming materials are selected from the group consisting of fibers, rods, mesh, particles, crystals and combinations thereof.

3. The mixture of claim 1 further including stable filler materials not generally soluble in vivo.

4. The mixture of claim 1 wherein the macropore forming materials include a mesh which dissolves to provide a cross-connected macroporous structure in a matrix of the hardened calcium phosphate compound.

5. The mixture of claim 1 wherein the mixture comprising the composite is comprised, at least in part, of separate, discrete regions of mixtures of the calcium phosphate compound and one of said macropore forming materials.

6. The mixture of claim 5 wherein the separate regions are adjacent layers.

7. The composite of claim 5 wherein the separate regions include an outside region and an adjacent inside region and wherein the dissolution rate of the outside region macropore forming material exceeds the dissolution rate of the inside region macropore forming material.

8. The mixture of claim 5 wherein at least two of said separate regions include macropore forming materials, the said macropore forming materials each having distinct geometric configurations.

9. The mixture of claim 5 wherein at least two separate regions include a combination of distinct macropore forming materials.

10. The mixture of claim 5 wherein the calcium phosphate compound is distinct in two distinct regions.

11. The mixture of claim 1 in the form of a bone replacement pre-form.

12. The mixture of claim 1 wherein the mixture is non-rigid.

13. The mixture of claim 1 wherein the mixture is elastomeric.

14. The mixture of claim 1 further including an additive selected from the group consisting of viscosity adjustment compounds, biologic compounds, pharmacologic compounds, marker compounds, sterilizing agents, accelerator compounds, at least one insoluble stable filler material, and combinations thereof.

15. The mixture of claim 1 wherein the calcium phosphate compound comprises a mixture of tetracalcium phosphate and dicalcium phosphate anhydrous.

16. The mixture of claim 1 wherein the calcium phosphate compound forms a hydroxyapatite-containing solid when exposed to water.

17. The mixture of claim 1 wherein at least one of the macropore forming materials is selected from the group consisting of mannitol, sodium phosphate, sodium bicarbonate, and mixtures thereof.

18. The mixture of claim 1 wherein at least one of the macropore forming materials comprises a gradient of dissolution rates in the mixture.

19. The mixture of claim 1 wherein the macropore forming materials comprise at least two separate, homogeneous sections in the mixture.

20. The mixture of claim 1 wherein the macropore forming materials comprise at least two separate sections, each section having a distinct gradient dissolution rate.

21. The mixture of claim 1 wherein the macropore forming materials comprise at least two separate sections in said mixture, one of said sections comprising a homogeneous dissolution rate section and another of said sections having a gradient dissolution rate.

22. The mixture of claim 1 wherein at least one of said macropore forming materials are selected from the group of fast dissolution rate materials consisting of glass, ceramics, polymers and combinations thereof.

23. A method of bone replacement comprising the steps of:
 (a) mixing the composition of any of claims 1–22; and
 (b) placing said mixture in vivo.

24. A method of hard tissue replacement comprising the steps of:
 (a) mixing the composition of any of claims 1–23; and
 (b) placing said mixture in vivo.

25. The mixture of claim 1 wherein said first macropore forming material is selected from the group consisting of fast dissolution rate materials, medium dissolution rate materials, slow dissolution rate materials, stable materials, and mixtures thereof and said second macropore forming material is selected from the group consisting of fast dissolution rate materials, medium dissolution rate materials, slow dissolution rate materials, stable materials and combinations thereof.

26. The mixture of claim 1 further including an additional additive selected from the group consisting of elastomeric agents, fast hardening agents, gelling agents, stable filler materials and combinations thereof.

27. The mixture of claim 26 wherein the elastomeric agent is selected from the group consisting of chitosan, chitosan derivatives and combinations thereof.

28. The mixture of claim 26 wherein the fast hardening agent is sodium phosphate solution.

29. The mixture of claim 26 wherein the gelling agent is selected from the group consisting of hydroxypropyl methylcellulose, carboxyl methylcellulose, starch, proteoglycans, glycoproteins and combinations thereof.

30. The mixture of claim 26 wherein the insoluble agent is selected from the group consisting of metal, carbon and combinations thereof.

31. The mixture of claim 1 wherein said calcium phosphate compound is selected from the group consisting of tetracalcium phosphate and dicalcium phosphate anhydrous cements, alpha-tricalcium phosphate cements, beta-tricalcium phosphate cements, dicalcium phosphate anhydrous cements, amorphous calcium phosphate cements and combinations thereof.

32. The mixture of claim 1 wherein at least one of said macropore forming materials is characterized by at least a medium dissolution rate in vivo.

33. The mixture of claim 1 wherein the macropore forming materials include meshes or fibers which dissolve to provide a cross-connected macroporous structure in a matrix of the hardened calcium phosphate compound, said cross-connected macroporous structure having interconnected cylindrical shapes from the dissolution of meshes or fibers to improve the tissue ingrowth process into the macroporous implant in vivo.

34. The mixture of claim 1 wherein said macropore forming materials are in combination characterized by increasing the flexural strength of said mixture.

35. The mixture of claim 1 wherein said macropore forming materials are in combination characterized by a dissolution rate greater than about one week in vivo.

36. The mixture of claim 1 wherein one of said macropore forming materials has a fast dissolution rate and another macropore forming material has a medium or slow dissolution rate.

37. A bone material and hard tissue replacement material comprising, in combination, a mixture of:
 a calcium phosphate compound that forms a chemically compatible in vivo bone or hard tissue replacement composition; and
 at least first and second macropore forming materials, said first and second macropore forming materials each having a dissolution rate in vivo, said materials in combination characterized by a dissolution rate greater than about one week in vivo.

38. The bone material and hard tissue replacement material of claim 37 wherein said combination of first and second macropore forming materials is characterized by increasing the flexural strength of said mixture in vivo by at least about one order of magnitude relative to a control comprising said compound.

39. The mixture of claim 1 wherein the first macropore forming material comprises, at least in part, said compound.

40. The bone material and hard tissue replacement material of claim 37 wherein said combination of first and second macropore forming materials is characterized by increasing the toughness of said combination by at least about two orders of magnitude relative to a control comprising said compound.

41. The mixture of claim 1 wherein the toughness of said mixture is increased by at least about two orders of magnitude relative to a control comprising said compound.

* * * * *